United States Patent [19]
Kondo et al.

[11] Patent Number: 6,031,084
[45] Date of Patent: Feb. 29, 2000

[54] AZOAMIDE COMPOUND

[75] Inventors: Suguru Kondo; Seiji Hirose; Kazuo Shiraki, all of Saitama, Japan

[73] Assignee: Wako Pure Chemical Industries, Ltd., Osaka, Japan

[21] Appl. No.: 09/307,717

[22] Filed: May 10, 1999

[30] Foreign Application Priority Data

May 12, 1998 [JP] Japan .................................. 10-146635

[51] Int. Cl.[7] .................................................. C07C 245/00
[52] U.S. Cl. ........................................... 534/886; 524/190
[58] Field of Search .............................. 534/886; 524/190

[56] References Cited

U.S. PATENT DOCUMENTS 5,001,228  3/1991  Shiraki et al. ...................... 534/886 X

FOREIGN PATENT DOCUMENTS 61-63643  4/1986  Japan .
2-149551  6/1990  Japan .

*Primary Examiner*—Fiona T. Powers
*Attorney, Agent, or Firm*—Armstrong, Westerman, Hattori, McLeland & Naughton

[57] ABSTRACT

A compound shown by the general formula [1]

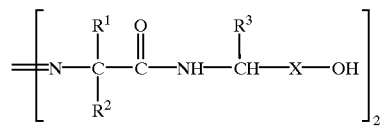

wherein $R^1$ and $R^2$ are independently a lower alkyl group or a cyano group, $R^3$ is a lower alkyl group and X is a lower alkylene group, showing high solubility into various kinds of polar solvents and are capable of effectively introducing hydroxy groups into terminal positions of polymers and their use.

8 Claims, No Drawings

AZOAMIDE COMPOUND

BACKGROUND OF THE INVENTION

The present invention relates to an azoamide compound showing high solubility into various kinds of polar solvents, and useful as a polymerization initiator, etc.

In polymer compounds, development has recently been moved from widely usable polymers into functional ones, and attention has been paid to block polymers which are expected to show effectively various kinds of functions.

Under such circumstances, there have been proposed such trials as obtaining block polymers by polycondensation of plural numbers of polymers having different properties with each other utilizing terminal functional groups of polymers which are produced by use of azo compounds having functional groups and obtaining block copolymers by using a linear polymeric azo compound which are produced by alternate polycondensation between azo compounds and bifunctional compounds or using polymeric azo compounds which are produced by polycondensation of two or more kinds of azo compounds having dual decomposition temperatures.

For these purposes, there have been studied on various kinds of azo compounds having reactive functional groups, such as 2,2'-azobis (2-cyanopentanol), 2,2'-azobis(2-cyanopentanoic acid) and an azo compound having a hydroxy group (JP-A 61-63643) etc.

However, there is a problem that a solvent solubility and a storage stability of those azo compounds are not sufficient, and thus actually no considerable effect has been attained.

SUMMARY OF THE INVENTION

The present invention has been conducted under the circumstances mentioned above and its object is to provide novel azo compounds having high solubility into various kinds of polar solvents and are capable of effectively introducing hydroxy groups into terminals of polymers.

The present invention relates to a compound shown by the general formula [1]

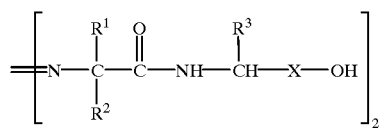

[1]

wherein $R^1$ and $R^2$ are independently a lower alkyl group or a cyano group, $R^3$ is a lower alkyl group and X is a lower alkylene group.

Further, the present invention relates to a polymerization initiator, which comprises the above azoamide compound.

Still further, the present invention relates to a method for polymerizing an α,β-ethylenically unsaturated monomer, which comprises using the above azoamide compound as a polymerization initiator.

DETAILED DESCRIPTION OF THE PREFERRED EMBODIMENTS

For the purpose of attaining the above mentioned objects, the present inventors have earnestly investigated novel azoamide compounds showing high solubility into various kinds of polar solvents and are capable of effectively introducing hydroxy groups into terminals of polymers.

The lower alkyl group shown by $R^1$, $R^2$ and $R^3$ in the general formula [1] may be independently straight chained, branched or cyclic and includes one having 1 to 5 carbon atoms, preferably 1 to 3 carbon atoms, more preferably 1 to 2 carbon atoms, which are specifically exemplified by a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, a sec-pentyl group, a neopentyl group, a 2-methylbutyl group, a 1-ethylpropyl group, a 2-ethylpropyl group, a cyclopropyl group, a cyclobutyl group, a cyclopentyl group, etc.

The lower alkylene group shown by X may be straight chained, branched or cyclic and includes one having 1 to 5 carbon atoms, preferably 1 to 3 carbon atoms, which are specifically exemplified by a methylene group, an ethylene group, a trimethylene group, a propylene group, a tetramethylene group, a pentamethylene group, a 2,2'-dimethylpropylene group, a 2-ethylpropylene group, a cyclopropylene group, a cyclopentylene group, etc.

The structural characteristic of the present compound shown by the general formula [1] is that the carbon atom binding to a nitrogen atom of the amido group is a secondary carbon atom.

The specific examples of the azoamide compound of the present invention shown by the above general formula [1] are as follows.

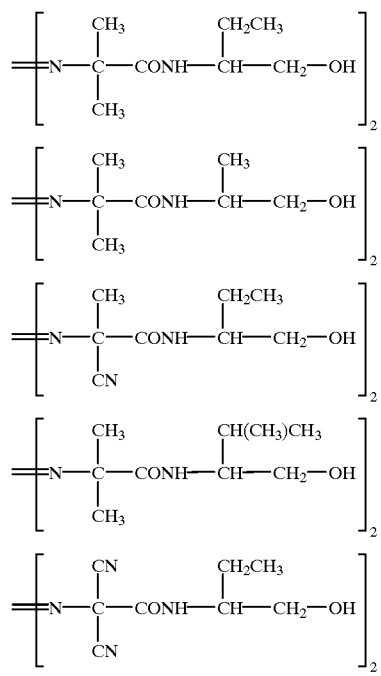

The azoamide compound of the present invention shown by the above general formula [1] can be obtained, for instance, by reacting an azodicarboxylic acid diester compound shown by the general formula [2]

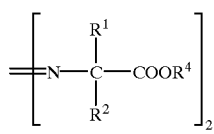

wherein $R^4$ is a lower alkyl group; $R^1$ and $R^2$ are the same as defined above, with an amino alcohol shown by the general formula [3]

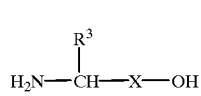

wherein $R^3$ and X are the same as defined above, in the absence or presence of a suitable solvent and in the presence of an organic alkaline metal compound.

The lower alkyl group shown by $R^4$ in the general formula [2] may be straight chained or branched and includes one having 1 to 5 carbon atoms, preferably 1 to 3 carbon atoms, which are specifically exemplified by a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a sec-pentyl group, a neopentyl group, etc.

The specific examples of the azodicarboxylic acid diester compound shown by the above general formula [2] are dimethyl 2,2'-azobis(2-metylpropionate), diethyl 2,2'-azobis (2-metylpropionate), dipropyl 2,2'-azobis(2-metylpropionate), dibutyl 2,2'-azobis (2-metylpropionate), dipentyl 2,2'-azobis(2-methylpropionate), dimethyl 2,2'-azobis (2-cyanopropionate), diethyl 2,2'-azobis(2-cyanopropionate), dimethyl 2,2'-azobis (2-cyanobutyrate), di-tert-butyl 2,2'-azobis(2-cyclobutylbutyrate), dicyclopentyl 2,2'-azobis (2-t-butylvarelate), etc.

The specific examples of the amino alcohol shown by the above general formula [3] are 3-amino-4-methylpentanol, 2-aminopropanol, 2-aminobutanol, 3-aminobutanol, 2-amino-2-cyclobutylethanol, 3-(1-amino-3,3-dimethylbutyl)cyclobutane-1-ol, etc.

The organic alkaline metal compound used in producing the azoamide compound of the present invention includes alkaline metal alkoxides such as sodium methoxide, sodium ethoxide, potassium methoxide, potassium ethoxide and potassium tert-butoxide; organolithium compounds such as n-butyl lithium and tert-butyl lithium, etc.

The reaction solvent includes hydrocarbons such as toluene, xylene and benzene; alcohols such as methanol, ethanol, n-propanol, isopropanol, n-butanol, isobutanol and tert-butanol; dimethylformamide, dimethylsulfoxide, etc. These solvents may be used alone or in a suitable combination of two or more thereof.

An amount of the amino alcohol to be used in producing the azoamide compound of the present invention depends on the kind of the amino alcohol to be used and it is generally 1.5 to 10 moles, preferably 2 to 5 moles per mole of the azodicarboxylic acid diester compound.

An amount of the organic alkaline metal compound depends on the kind of the amino alcohol to be used and it is generally 0.05 to 3 equivalents, preferably 0.1 to 0.5 equivalents to the azodicarboxylic acid diester compound.

Reaction temperature is not specifically limited, but when it is too high, azo groups are decomposed, and when it is too low, the reaction speed becomes low so that a longer reaction time is required, and thus it is generally 0 to 40° C.

A reaction time depends on the kind of the azodicarboxylic acid compound or the amino alcohol, and it is generally 1 to 24 hours.

Reaction operations and after-treatments other than the above may be any of conventional ones in a similar kind of reaction.

As the azodicarboxylic acid diester compound shown by the general formula [2] and the amino alcohol shown by the general formula [3] which are used in producing the azoamide compound of the present invention shown by the general formula [1], commercially available one may be used or one obtained by synthesizing after a conventional manner may be used.

Thus obtained azoamide compound of the present invention can easily give radicals together with nitrogen gas by decomposition of the azo group on heating or irradiation of lights, and therefore when a various kind of polymerizable monomers coexist in the system, this monomer can rapidly be polymerized.

Polymerization or copolymerization of polymerizable monomers using the azoamide compound of the present invention as a polymerization initiator can be realized by subjecting the azoamide compound of the present invention and the polymerizable monomer to a polymerization reaction in the absence or presence of a suitable solvent, if necessary, under inert gas atmosphere, after a conventional manner.

The above polymerizable monomer includes an α,β-ethylenically unsaturated monomer shown by the general formula [4]

wherein $R^5$ is a hydrogen atom, a lower alkyl group, a carboxyl group, a carboxyalkyl group, an alkyloxycarbonyl group, a hydroxyalkyloxycarbonyl group, a cyano group or an aldehyde group, $R^6$ is a hydrogen atom, a lower alkyl group, a carboxyl group, an alkyloxycarbonyl group, a hydroxyalkyloxycarbonyl group, a cyano group or a halogen atom, $R^7$ is a hydrogen atom, a lower alkyl group, a haloalkyl group, a hydroxy group, an aryl group which may have a substituent, an aliphatic heterocyclic group, an aromatic heterocyclic group, a halogen atom, an alkyloxycarbonyl group, a hydroxyalkyloxycarbonyl group, a sulfonic acid group, a cyano group, a cyano-containing alkyl group, an acyloxy group, a carboxyl group, a carboxyalkyl group, an aldehyde group, an amino group, an aminoalkyl group, a carbamoyl group, an N-alkylcarbamoyl group or a hydroxyalkyl group, and $R^5$ and $R^6$ may combine with each other to form an aliphatic ring together with neighboring —C=C—.

The lower alkyl group shown by $R^5$ to $R^7$ in the general formula [4] may be straight chained, branched or cyclic and includes one having 1 to 6 carbon atoms, which are specifically exemplified by a methyl group, an ethyl group, an n-propyl group, an isopropyl group, an n-butyl group, an isobutyl group, a tert-butyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group, etc.

The carboxyalkyl group shown by $R^5$ and $R^7$ includes the lower alkyl group mentioned above whose hydrogen atom is substituted by a carboxyl group, and are specifically exemplified by a carboxymethyl group, a carboxyethyl group, a carboxypropyl group, a carboxybutyl group, a carboxypentyl group, a carboxyhexyl group, etc.

The alkyloxycarbonyl group shown by $R^5$ to $R^7$ includes one having 2 to 11 carbon atoms, which are specially exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group, a decyloxycarbonyl group, etc.

The hydroxyalkyloxycarbonyl group shown by $R^5$ to $R^7$ includes the alkyloxycarbonyl group having 2 to 11 carbon atoms mentioned above whose hydrogen atom is substituted by a hydroxy group, and are specifically exemplified by a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group, a hydroxydecyloxycarbonyl group, etc.

The halogen atom shown by $R^6$ and $R^7$ includes fluorine, chlorine, bromine and iodine.

The haloalkyl group shown by $R^7$ includes one obtained by halogenating (fluorinating, chlorinating, brominating, iodinating, etc.) the lower alkyl group having 1 to 6 carbon atoms mentioned above, and are specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, etc.

The aryl group in the aryl group which may have a substituent includes a phenyl group, a tolyl group, a xylyl group, a naphtyl group, etc., and the substituent includes an amino group, a hydroxy group, a lower alkoxy group, a carboxyl group, sulfonic acid group, etc., and the substituted aryl group is specifically exemplified by an aminophenyl group, a toluidino group, a hydroxyphenyl group, a methoxyphenyl group, a t-butoxyphenyl group, a carboxyphenyl group, a sulfophenyl group, etc.

The aliphatic heterocyclic group includes preferably 5- or 6-membered one containing 1 to 3 hetero atoms such as nitrogen atom, oxygen atom and sulfur atom and is specifically exemplified by a pyrrolidyl group, a pyrrolidyl-2-one group, a piperidyl group, a piperidino group, a piperazinyl group, a morpholino group, etc.

The aromatic heterocyclic group includes preferably 5- or 6-membered one containing 1 to 3 hetero atoms such as nitrogen atom, oxygen atom and sulfur atom and is specifically exemplified by a pyridyl group, an imidazolyl group, a thiazolyl group, a furanyl group, a pyranyl group, etc.

The cyano-containing alkyl group includes the lower alkyl group mentioned above whose hydrogen atom is substituted by a cyano group and is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group includes one having 2 to 20 carbon atoms derived from a carboxylic acid and is specifically exemplified by an acetyloxy group, a propionyloxy group, a butylyloxy group, a pentanoyloxy group, a hexanoyloxy group, a heptanoyloxy group, an octanoyloxy group, a nonanoyloxy group, a decanoyloxy group, a benzoyloxy group, etc.

The aminoalkyl group includes the lower alkyl group mentioned above whose hydrogen atom is substituted by an amino group and is specifically exemplified by an aminomethyl group, an aminoethyl group, an aminopropyl group, an aminobutyl group, an aminopentyl group, an aminohexyl group, etc.

The N-alkylcarbamoyl group includes a carbamoyl group whose hydrogen atom is substituted by an alkyl group and is specifically exemplified by an N-methylcarbamoyl group, an N-ethylcarbamoyl group, an N-n-propylcarbamoyl group, an N-isopropylcarbamoyl group, an N-n-butylcarbamoyl group, an N-tert-butylcarbamoyl group, etc.

The hydroxyalkyl group includes the lower alkyl group mentioned above whose hydrogen atom is substituted by a hydroxy group and is specifically exemplified by a hydroxymethyl group, a hydroxyethyl group, a hydroxypropyl group, a hydroxybutyl group, a hydroxypentyl group, a hydroxyhexyl group, etc.

The aliphatic ring formed by $R^5$, $R^6$ and —C=C— includes an unsaturated aliphatic ring having 5 to 10 carbon atoms and the ring may be monocyclic or polycyclic, which is specifically exemplified by a norbornene ring, a cyclopentene ring, a cyclohexene ring, a cyclooctene ring, a cyclodecene ring, etc.

The specific examples of the α,β-ethylenically unsaturated monomer shown in the general formula [4] are ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene, 4-ethylstyrene, divinyl benzene; alkenylesters having 3 to 20 carbon atoms such as vinyl formate, vinyl acetate, vinyl propionate and isopropenyl acetate; halogen-containing ethylenically unsaturated compounds having 2 to 20 carbon atoms such as vinyl chloride, vinylidene chloride, vinylidene fluoride; ethylenically unsaturated carboxylic acids having 3 to 20 carbon atoms such as acrylic acid, methacrylic acid, itaconic acid, maleic acid, fumaric acid, crotonic acid, vinylacetic acid, allylacetic acid, vinylbenzoic acid (each of these acids may be in the form of a salt such as an alkaline metal salt (e.g. a sodium salt or a potassium salt), an ammonium salt or the like); ethylenically unsaturated carboxylic acid esters having 4 to 20 carbon atoms such as methyl methacrylate, ethyl methacrylate, propyl methacrylate, butyl methacrylate, 2-ethylhexyl methacrylate, stearyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate; ethylenically unsaturated cyano-containing compounds having 3 to 20 carbon atoms such as acrylonitrile, methacrylonitrile and allylcyanide; ethylenically unsaturated amide compounds having 3 to 20 carbon atoms such as acrylamide and methacrylamide; ethylenically unsaturated aldehydes having 3 to 20 carbon atoms such as acrolein and croton aldehyde; ethylenically unsaturated sulfonic acids such as vinyl sulfonic acid and 4-vinylbenzene sulfonic acid (each of these acids may be in form of a salt, for example, an alkaline metal salt such as sodium salt and potassium salt); ethylenically unsaturated aliphatic amines having 2 to 20 carbon atoms such as vinylamine and allylamine; ethylenically unsaturated aromatic amines having 8 to 20 carbon atoms such as vinyl aniline; ethylenically unsaturated aliphatic heterocyclic amines having 5 to 20 carbon atoms such as N-vinylpyrrolidone and vinyl piperidine; ethylenically unsaturated aromatic heterocyclic amines having 5 to 20 carbon atoms such as vinyl pyridine and 1-vinylimidazole;

ethylenically unsaturated alcohols having 3 to 20 carbon atoms such as allyl alcohol and crotyl alcohol; ethylenically unsaturated phenols having 8 to 20 carbon atoms such as 4-vinylphenol, etc.

As the polymerization initiator in the polymerization reaction, the azoamide compound of the present invention may be used alone or a combination of two or more thereof.

Further, one or more of a polymerization initiator other than the azoamide compound of the present invention may be co-used with one or more of the azoamide compound of the present invention.

The polymerization initiator other than the azoamide compound of the present invention includes azo compounds such as azobisisobutyronitrile, 2,2'-azobis(2,4-dimethylvaleronitrile), 2,2'-azobis (2-amidinopropane) dihydrochloride, 2,2'-azobis[2-(2-imidazolin)-2-yl]propane, 2,2'-azobisisobutylamide dihydrate, dimethyl 2,2'-azobis (2-methylpropionate) and 4,4'-azobis(4-cyanovaleric acid), organic peroxide compounds such as benzoyl peroxide and di-tert-butyl peroxide, photo polymerization initiators such as benzoin ethyl ether.

The polymerization method includes solution polymerization, bulk polymerization, suspension polymerization, emulsion polymerization, etc.

The reaction solvent includes ethers such as tetrahydrofuran, diethylether and dioxane, halogenated hydrocarbons such as chloroform, methylene chloride and 1,2-dichloroethane, hydrocarbons such as toluene, benzene and xylene, alcohols such as methanol, ethanol and isopropanol, ketones such as acetone, 2-butanone and isobutylmethylketone, acetonitrile, N,N-dimethylformamide, dimethylsulfoxide, water, etc.

Those solvents may be used alone or in a suitable combination of two or more thereof.

In the emulsion polymerization, a conventional surfactant may be used.

The polymerization reaction is preferably conducted under inert gas atmosphere, and the inert gas includes nitrogen gas, argon gas, etc.

An amount of the azoamide compound of the present invention to be used in the above polymerization reaction depends on the kind of the polymerizable monomer to be used, and when the azoamide compound of the present invention is used alone, the amount is 0.01 to 100 wt %, preferably 0.05 to 50 wt % to the polymerizable monomer. When the azoamide compound of the present invention is co-used with other polymerization initiator, the ratio of the both compounds is suitably selected taking the kind of the polymerization initiator, the kind of the polymerizable monomer, the desired characteristics of the resulting polymer, etc. into consideration.

A concentration of the polymerizable monomer in the solvent on the polymerization reaction depends on the kind of the polymerizable monomer, and it is generally 5 to 100 wt % (no solvent), preferably 10 to 60 wt %.

A polymerization temperature is not specially limited, but when it is too low, the polymerization slowly proceed as a result of which little decomposition of azo groups is caused and on the other hand, when it is too high, controlling of the polymerization is difficult as a result of which too much decomposition of azo groups is caused, and it is generally 20 to 150° C., preferably 50 to 130°C.

A polymerization time depends on reaction conditions such as a reaction temperature, the kinds of the polymerizable monomer and the azoamide compound of the present invention to be used and concentrations of those reactants, and it is generally 2 to 24 hours.

The azoamide compound of the present invention has hydroxy groups at the terminal position and the carbon atom combining with a nitrogen atom of the amido group is a secondary carbon atom, and therefore, the compound shows high solubility in high polar solvents such as water and methanol and also in comparatively low polar organic solvents.

Comparing with the solubility of the azoamide compound having hydroxy group which has so far used as a polymerization initiator such as 2,2'-azobis[2-methyl-N-(2-hydroxyethyl)-propionamide] whose carbon atom combining with a nitrogen atom of the amido group is a primary carbon atom and 2,2'-azobis{2-methyl-N-[1,1-bis (hydroxymethyl)-2-hydroxyethyl]propionamide} whose carbon atom combining with a nitrogen atom of the amido group is a tertiary carbon atom, the solubility of the azoamide compound of the present invention is higher into the various kinds of polar solvents.

High solubility of a polymerization initiator in solvents can expand the choices of monomers capable of being polymerized by using the polymerization initiator and of solvents to be used. Further this characteristic makes it possible to dissolve the initiator in a reaction solution in high concentration, which is led to get a lot of scale merits, and this characteristic is accompanied with such a merit as capable of adding the initiator in a solution state into the reactor for the polymerization.

The azoamide compound of the present invention can be used as a polymerization initiator for various polymerization methods such as solution polymerization, bulk polymerization, suspension polymerization and emulsion polymerization, etc., and be used for polymerization of various ethylenically unsaturated monomers capable of being polymerized by radical polymerization.

Moreover, with the use of the azoamide compound of the present invention, it is possible to reduce an amount of a non-reacted monomer contained in the resulting polymer or oligomer or the resulting polymer composition. The use of the polymer or the oligomer which are obtained by polymerization with the use of the compound of the present invention can be used for preparations of paints, inks, toner binders, fibers or their modifiers, coating agents, flocculants, cosmetic materials, sizing agents, tackifiers, adhesives, etc.

The azoamide compound of the present invention has hydroxy groups at their terminal positions, and therefore, other kinds of novel azoamide compound can be given by reacting the azoamide compound of the present invention with a compound having functional groups which can react with hydroxy groups of the azoamide compound of the present invention. The other novel azoamide compounds include macro azo initiators comprising a repeating unit having a lot of azo groups in their molecular, azoamide compounds having a group such as an acrylic group, a methacrylic group or an allyl group which can be obtained by reaction of the azoamide compound of the present invention with an acid chloride, azoamide compounds which can be obtained by reaction of the azoamide compound of the present invention with a γ-isocyanate alkoxysilane, etc.

The hydroxy group originated from the azoamide compound of the present invention can be introduced into terminals of a polymer which is obtained by using the present azoamide compound.

The use of the polymer having hydroxy groups in their terminal positions includes materials of resins such as polyester resin, polycarbonate resin and polyurethane resin, paints, adhesives, inks, various block polymers, etc.

The polymer having the functional group is useful as material for synthesizing a macromonomer etc. Moreover, the use of the azoamide compounds of the present invention includes photopolymerization initiators, radical generating agents can be used various organic reactions, etc.

The functional group such as a silyl group, a vinyl group and an epoxy group can be introduced into the terminal hydroxy groups of the polymer mentioned above by utilizing a known organic reaction.

In the following, the present invention is further explained referring to Examples and Experiments, but the present invention is not limited thereto by any means.

EXAMPLE

Example 1

Synthesis of 2,2'-azobis[N-(butanol-2-yl)-2-methylpropionamide]

To a mixture of 23.0 g of dimethyl 2,2'-azobis (2-methylpropionate), 19.6 g of (R)-(-)-2-amino-1-butanol and 10 ml of methanol was added 4.25 g of 28% sodium methoxide solution, followed by reaction at room temperature for 7 hours. After keeping standing overnight, 100 ml of water was added to the reaction solution and the reactant was extracted by 100 ml of methylene chloride. The extract was washed and dried under reduced pressure to give 25.8 g of crude crystals. The crude crystals were dissolved in 65 ml of acetone and were recrystallized by adding 140 ml of n-hexane. The resulting crystal was recovered by filtration and dried to give 18.7 g of pale yellow-white powdery crystal of 2,2'-azobis[N-(butanol-2-yl)-2-methylpropionamide].

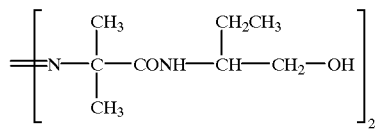

mp: 79.5° C. (dec). $^1$HNMR δ ppm(CDCl$_3$): 0.94(6H, t, —CH$_2$CH$_3$), 1.39(12H, s, —CH$_3$), 1.60(4H, m, —CH$_2$CH$_3$), 3.61(4H, m, —CH$_2$OH), 3.91(2H, br, —NHCH) UV: λ max 375 nm($E_{1\%}$=0.985/MeOH). 10 hours half life temperature=84.7° C.

Example 2

Synthesis of 2,2'-azobis[N-(propanol-2-yl) 2-methylpropionamide]

To a mixture of 23.0 g of dimethyl 2,2'-azobis (2-methylpropionate), 16.5 g of (±)-2-amino-1-propanol and 10 ml of methanol was added 4.25 g of 28% solution of sodium methoxide, followed by reaction at room temperature. After the reaction, the reaction solution was cooled and poured into 20 ml of water. The precipitated crystal was ifiltrated, washed and dried to give 24.2 g of pale yellow-white powdery crystal of 2,2'-azobis[N-(propanol-2-yl)-2-methylpropionamide]

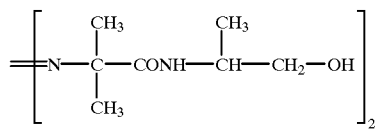

mp: 141° C. (dec). $^1$HNMR δ ppm (CD$_3$OD): 1.28 (6H, dd, —CHCH$_3$), 1.47 (12H, s, —CH$_3$), 3.63 (4H, d, —CH$_2$OH), 4.12 (2H,br, —NHCH) UV: λ max 375 nm($E_{1\%}$=1.057/ MeOH). 10 hours half life temperature=83.1° C.

Experiment 1

Measurement of Solubility

Solubilities of 2,2'-azobis[N-(butanol-2-yl)-2-methylpropionamide] (hereinafter abbreviated as Present compound 1) obtained by Example 1 and 2,2'-azobis[N-(propanol-2-yl)-2-methylpropionamide] (hereinafter abbreviated as Present compound 2) obtained by Example 2 to various kinds of polar solvent was measured. The result is shown in Table 1.

Experiment 2~4

Measurement of Solubility

The same measurement of solubility as Experiment 1 was conducted except for using of 2,2'-azobis[2-methyl-N-(2-hydroxyethyl)-propionamide]

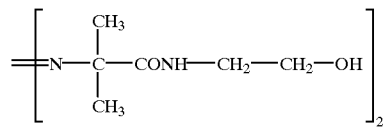

(hereinafter abbreviated as Known compound 1), 2,2'-azobis {2-methyl-N-[1,1-bis(hydroxymethyl)-2-hydroxyethyl] propionamide}

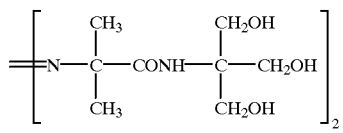

(hereinafter abbreviated as Known compound 2) and 2,2'-azobis {2-methyl-N-[1,1-bis(hydroxymethyl)ethyl] propionamide}

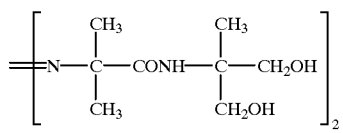

(hereinafter abbreviated as Known compound 3) in place of Present compound 1. The result is also shown in Table 1.

TABLE 1

| | Measurement of Solubility | | | | |
|---|---|---|---|---|---|
| Solvent | Present compound 1 | Present compound 2 | Known compound 1 | Known compound 2 | Known compound 3 |
| Water | 10 g< | 0.6 g | 2.4 g | 2.0 g | 0.6 g |
| Methanol | 10 g< | 6.5 g | 4.55 g | 1.89 g | 5.18 g |
| Acetone | 10 g< | 0.3 g | insoluble | insoluble | insoluble |
| Tetrahydrofuran | 10 g< | 0.3 g | insoluble | insoluble | insoluble |
| 2-butanol | 10 g< | 0.1 g> | insoluble | insoluble | insoluble |

As is clear from the result of Table 1, it can be understood that Present compound 1 and 2 obtained in the Examples are soluble also in rather low polar solvents such as 2-butanol. Moreover, the solubilities of Present compounds 1 and 2 in a various kind of polar solvents are remarkably higher than that of Known compounds 1, 2 and 3.

That is, the solubilities of azoamide compounds in which the carbon atom bound to a nitrogen atom of the amido group is a secondary carbon atom are clearly higher in various kind of solvents as compared with those in which the said carbon atom is a primary or a tertiary carbon atom.

Example 3

Acrylamide(20 g) was dissolved in 380 g of distilled water and 14.0×10⁵ mol of Present compound 1 obtained in Example 1 was added thereto as a polymerization initiator. The mixture was heated at 80° C. with stirring under nitrogen gas atmosphere to cause polymerization reaction. After the polymerization was started, samplings of the reaction solution were conducted at predetermined intervals, and methanol was added to the samples to form precipitates of the produced polymer, which were recovered and dried. The polymerization rates at each sampling time were measured. The results are shown in Table 2.

TABLE 2

| | Polymerization rates at polymerization time (%) | | | | | |
|---|---|---|---|---|---|---|
| | Polymerization time | | | | | |
| Initiator | 0.5 H | 1.0 H | 1.5 H | 2.0 H | 3.0 H | 4.0 H |
| Present compound 1 | 26.1 | 42.0 | 54.4 | 65.1 | 76.1 | 82.9 |
| Known compound 1 | 26.9 | 45.9 | 56.0 | 67.6 | 76.2 | 82.1 |
| Known compound 2 | 14.7 | 31.0 | 35.4 | 43.2 | 55.6 | 66.1 |
| Known compound 3 | 15.7 | 26.9 | 33.6 | 40.6 | 53.8 | 64.2 |

Comparative Example 1~3

The polymerization rates were measured by same measurement as Example 3 except for using Known compound 1, Known compound 2 or Known compound 3 in place of using Present compound 1. The results are also shown in Table 2.

Table 2 shows that the polymerization rates on using Present compound 1 as a polymerization initiator is almost same or higher than that of the case of using Known compounds as a polymerization initiator.

As explained above, the present invention is to provide novel azoamide compounds showing high solubility into various kinds of polar solvents.

Further, polymers obtained by using the azoamide compounds of the present invention as a polymerization initiator have hydroxy groups originated from said azoamide compound at the terminal positions, and thus they can show various kinds of functions.

What is claimed is:

1. A compound shown by the general formula [1]

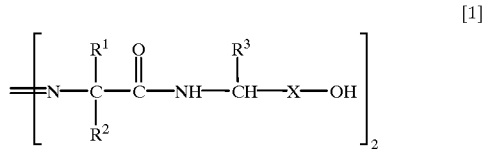

(wherein $R^1$ and $R^2$ are independently a lower alkyl group or a cyano group, $R^3$ is a lower alkyl group and X is an alkylene group).

2. The compound according to claim 1, wherein $R^1$, $R^2$ and $R^3$ are independently a lower alkyl group having 1 to 5 carbon atoms.

3. The compound according to claim 1, wherein X is a lower alkylene group having 1 to 5 carbon atoms.

4. The compound according to claim 1, wherein both $R^1$ and $R^2$ are a methyl group.

5. The compound according to claim 1, wherein $R^3$ is a methyl group, an ethyl group or an isopropyl group.

6. The compound according to claim 1, wherein X is a methylene group or an ethylene group.

7. A polymerization initiator, which comprises the compound as claimed in claim 1.

8. A method for polymerizing α,β-ethylenically unsaturated monomer, which comprises using the compound as claimed in claim 1 as a polymerization initiator.

* * * * *